(12) United States Patent
Kang et al.

(10) Patent No.: US 9,562,071 B2
(45) Date of Patent: Feb. 7, 2017

(54) METHOD FOR PREPARING EPTIFIBATIDE

(71) Applicant: HYBIO PHARMACEUTICAL CO., LTD., Shenzhen, Guangdong (CN)

(72) Inventors: Xu Kang, Shenzhen (CN); Jian Liu, Shenzhen (CN); Yaping Ma, Shenzhen (CN); Jiancheng Yuan, Shenzhen (CN)

(73) Assignee: HYBIO PHARMACEUTICAL CO., LTD., Shenzhen (CN)

( * ) Notice: Subject to any disclaimer, the term of this patent is extended or adjusted under 35 U.S.C. 154(b) by 0 days.

(21) Appl. No.: 14/392,203

(22) PCT Filed: Jun. 16, 2014

(86) PCT No.: PCT/CN2014/079935
§ 371 (c)(1),
(2) Date: Dec. 23, 2015

(87) PCT Pub. No.: WO2014/206210
PCT Pub. Date: Dec. 31, 2014

(65) Prior Publication Data
US 2016/0222059 A1   Aug. 4, 2016

(30) Foreign Application Priority Data
Jun. 27, 2013 (CN) .......................... 2013 1 0263341

(51) Int. Cl.
| | | |
|---|---|---|
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 7/06* | (2006.01) | |

(52) U.S. Cl.
CPC ...................................... *C07K 7/06* (2013.01)

(58) Field of Classification Search
CPC .......... A61K 38/00; A61K 38/08; C07K 7/06; C07K 7/64; C07K 7/56
See application file for complete search history.

(56) References Cited

U.S. PATENT DOCUMENTS
2006/0036071 A1   2/2006  Ho et al.

FOREIGN PATENT DOCUMENTS
| | | |
|---|---|---|
| CN | 101538316 | 9/2009 |
| CN | 101838308 | 9/2010 |
| CN | 102702320 | 10/2012 |
| CN | 103408637 | 11/2013 |

OTHER PUBLICATIONS

PCT International Search Report and Written Opinion issued in International Application No. PCT/CN2014/079935, dated Sep. 19, 2014. (English translation of Chinese text).
Takahashi et al., "Novel diphenylmethyl-derived amide protecting group for efficient liquid-phase peptide synthesis: AJIPHASE," *Organic Letters*, 14(17):4514-4517, 2012.

*Primary Examiner* — Hasan Ahmed
*Assistant Examiner* — Kaipeen Yang
(74) *Attorney, Agent, or Firm* — Parker Highlander PLLC

(57) ABSTRACT

Provided is a method for preparing eptifibatide, wherein the method comprises: obtaining an eptifibatide refined peptide solution; and obtaining and freeze-drying an eptifibatide refined peptide concentrate after rotary evaporation of the eptifibatide refined peptide solution, wherein the concentration of the eptifibatide refined peptide concentrate is 15-30 mg/ml and the temperature of rotary evaporation is 251° C.-35° C. The preparation method of the eptifibatide refined peptide solution is as follows: coupling Cys with a resin to obtain a Cys-resin; obtaining a polypeptide having a sequence as represented by SEQ ID NO: 1 by gradually coupling the Cys-resin with Pro, Trp, Asp, Gly, Har and Mpa; and obtaining the eptifibatide refined peptide solution through oxidation, cleavage, purification and transfer to salt.

2 Claims, 5 Drawing Sheets

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa = Har, Homoarginyl
<220> FEATURE:
<221> NAME/KEY: MOD_RES
<222> LOCATION: (7)..(7)
<223> OTHER INFORMATION: Xaa = Mpa, Mercaptopropanoic acid

<400> SEQUENCE: 1
```

-continued

```
Cys Pro Trp Asp Gly Xaa Xaa
1               5
```

METHOD FOR PREPARING EPTIFIBATIDE

The present application is a national phase application under 35 U.S.C. §371 of International Application No. PCT/CN2014/079935, filed Jun. 16, 2014, which claims the priority of Chinese Patent Application No. 201310263341.3, entitled "METHOD FOR PREPARING EPTIFIBATIDE", filed on Jun. 27, 2013 with the State Intellectual Property Office of the People's Republic of China, the entire contents of each of which are incorporated herein by reference.

Pursuant to 37 C.F.R. 1.821(c), a sequence listing is submitted herewith as an ASCII compliant text file on a compact disc named UNITP0010US_ST25.txt, created on Dec. 23, 2015 and having a size of ~1 KB. The content of the aforementioned file is hereby incorporated by reference in its entirety.

FIELD OF THE INVENTION

The invention relates to the field of the preparation of polypeptide, in particular to a method for preparing eptifibatide.

BACKGROUND OF THE INVENTION

Thrombotic disease is a common cardiovascular and cerebrovascular disease, and includes a variety of diseases in which the stenosis and occlusion of blood vessel lumens caused by thrombus lead to ischemia and infarction of main organs, thereby causing dysfunctions, and is usually manifested by myocardial infarction, ischemic cerebral infarction and venous thromboembolism. The disease can involve various organs and systems of the whole body, and has greatly high morbidity, disability rate and mortality. About 3% of people develops different forms of thrombotic diseases each year, which severely threaten the health of human beings. According to statistics, more than 3,000,000 people die from cardiovascular and cerebrovascular diseases in our country every year, with 75% of surviving patients suffering from disability, in which more than 40% suffer from serious disability.

Currently, drugs for treating thrombotic diseases are mainly devided into three categories in clinical practice: antiplatelet drugs, thrombolytic drugs and anticlotting drugs. Among them, antiplatelet drugs refer to drugs with the function of inhibiting the adhesion, aggregation and release of platelets, which inhibit aggregation of platelets and thus avoid formation of thrombus, and can effectively prevent the development of a cardiovascular and cerebrovascular disease and prolong the survival time of a patient. Such drugs include aspirin, dipyridamole, prostacyclin, ticlopidine, a platelet membranous gpIIb/IIIa receptor antagonist, an adenosine diphosphate receptor antagonist, ozagrel, clopidogrel, clopidogrel sulfate, etc. Among them, the platelet membranous gpIIb/IIIa receptor antagonist can inhibit the aggregation of platelets through inhibiting the binding of gpIIb/IIIa receptor to fibrinogen.

Eptifibatide is one of the platelet membranous gpIIb/IIIa receptor antagonist drugs, which is a small molecular heptapeptide with a structure as shown in Formula I. It contains a modified arginine-glycine-aspartic acid (RGD) sequence, has high selectivity, can decompose quickly after blockage of the receptor, and have advantages of strong antiplatelet effect, rapid onset and less adverse reactions, thus having good market prospect.

Various impurities will be produced during the preparation of eptifibatide. The existence of impurities will have certain influence on safety and effectiveness of the drug, in which dimer impurities have greater influence on the drug quality. The dimer of eptifibatide has two structures as shown in Formulae II and III. The existence of the dimer will reduce the optical purity of the raw material of eptifibatide, and meanwhile affect the solubility thereof. Studies have shown that eptifibatide dimer impurities are mainly formed at two stages. The first stage is during the synthesis of eptifibatide. At present, a non-oriented strategy is mainly employed in synthesis of eptifibatide, in which a linear peptide is firstly prepared with solid-phase synthesis, and the linear peptide is further oxidized to obtain a cyclopeptide. During the oxidization of the linear peptide, in addition to the target product via intra-chain cyclization, dimer impurities via inter-chain cyclization will also be formed. Due to the great difference between eptifibatide and the dimer impurities thereof in properties, the dimer impurities produced during the oxidization can be removed by reverse-phase HPLC purification and other methods. The second stage generating impurities is during concentration of a refined peptide. During concentration of a refined peptide, the disulfide bond of eptifibatide easily breaks down to form an inter-dimer disulfide bond, thus forming a dimer structure. Because of the difficulty in removing the dimer impurities produced at this stage, it is especially important to determine and control eptifibatide dimer impurities produced at this stage. Up to now, there is no research report about any method of controlling the eptifibatide dimer impurities during the concentration, and it is always a challenge to figure out how dimer impurities form and how to control the formation of dimer impurities in the field of polypeptide preparation. Thus, provision of a preparation method which can control formation of eptifibatide dimers is of important and practical significance.

Formula I

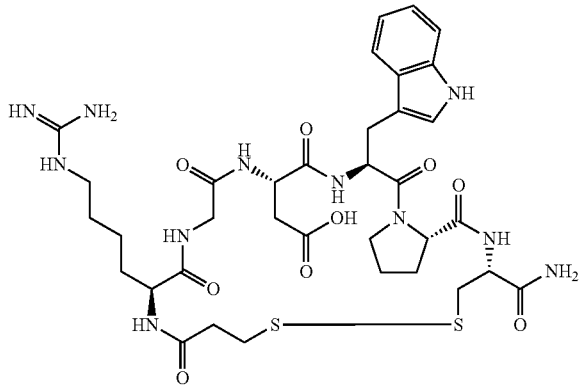

Formula II

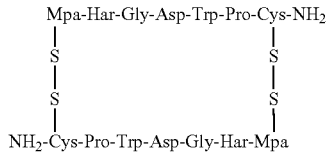

Formula III

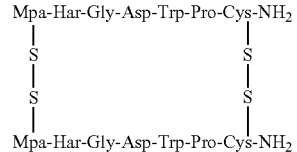

SUMMARY OF THE INVENTION

In view of the above, the present invention provides a method for preparing eptifibatide. This method significantly reduces the formation of eptifibatide dimer impurities by controlling the concentration and temperature during the concentration of the eptifibatide solution; and besides, allows acetonitrile and other organic residues to meet relevant standards in Chinese Pharmacopoeia.

To realize the above object, the following technical solutions are provided:

The present invention provides a method for preparing eptifibatide comprising:

step A: obtaining a refined eptifibatide peptide solution;

step B: rotarily evaporating the refined eptifibatide peptide solution, obtaining and freeze-drying a refined eptifibatide peptide concentrate;

wherein the concentration of the refined eptifibatide peptide concentrate is 15-30 mg/mL;

the temperature of the rotary evaporation is 25° C.-35° C.;

wherein the refined eptifibatide peptide solution is prepared by: obtaining a Cys-resin by coupling Cys to a resin; obtaining a polypeptide having a sequence as represented by SEQ ID NO: 1 by sequentially coupling the Cys-resin with Pro, Trp, Asp, Gly, Har and Mpa; and obtaining the refined eptifibatide peptide solution through oxidation, cleavage, purification and salt conversion.

Preferably, the concentration of the refined eptifibatide peptide concentrate is 15-20 mg/mL.

Preferably, the temperature of rotary evaporation is 30° C.-35° C.

In some examples of the present invention, the refined eptifibatide peptide concentrate accounts for 20%-36% by volume of the refined eptifibatide peptide solution.

The present invention provides a method for preparing eptifibatide. The method comprises: obtaining a refined eptifibatide peptide solution; rotarily evaporating the refined eptifibatide peptide solution, obtaining and freeze-drying a refined eptifibatide peptide concentrate; wherein the concentration of the refined eptifibatide peptide concentrate is 15-30 mg/mL; the temperature of the rotary evaporation is 25° C.-35° C.; wherein the refined eptifibatide peptide solution is prepared by obtaining a Cys-resin by coupling Cys to a resin, obtaining a polypeptide having a sequence as represented by SEQ ID NO: 1 by sequentially coupling the Cys-resin with Pro, Trp, Asp, Gly, Har and Mpa, and obtaining the refined eptifibatide peptide solution through oxidation, cleavage, purification and salt conversion. The method of the present invention controls the content of eptifibatide dimer impurities in the refined eptifibatide peptide concentrate to 0.01%-0.09% by controlling the concentration and temperature during the concentration of the eptifibatide solution. The content of the eptifibatide dimer impurities is within the limit for polypeptide impurities as established by FDA and SFDA. Besides, acetonitrile and other organic residues in the refined eptifibatide peptide concentrate meet relevant standards in Chinese Pharmacopoeia. However, in control experiments, when the temperature of rotary evaporation is too low and the concentration of the refined eptifibatide peptide concentrate is relatively low, although the content of the eptifibatide dimer impurities will not increase, the content of acetonitrile in the final product will go beyond the standards remarkably; when the temperature of rotary evaporation is too high and the concentration of the refined eptifibatide peptide concentrate is relatively low or high, the content of eptifibatide dimer impurities in the refined eptifibatide peptide concentrate will go beyond the limit of polypeptide impurities content as established by FDA and SFDA; and when the temperature of rotary evaporation is too low and the concentration of the refined eptifibatide peptide concentrate is relatively low, although the content of eptifibatide dimer impurities will not increase, the content of acetonitrile in the final product will go beyond the standards. It can be seen that the method for preparing eptifibatide of the present invention can significantly reduce the formation of eptifibatide dimer impurities, and besides, allow acetonitrile and other organic residues to meet relevant standards in Chinese Pharmacopoeia.

DETAILED DESCRIPTION OF THE INVENTION

Figure 1:
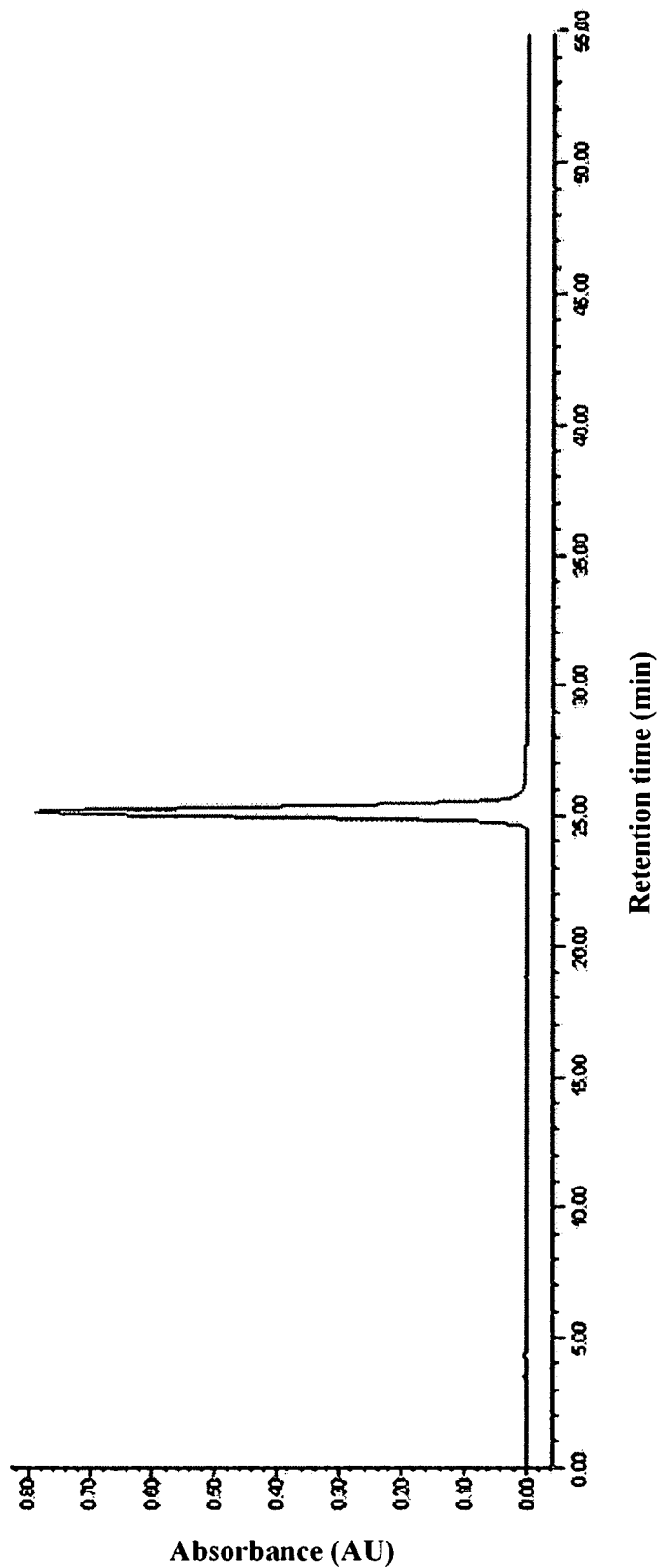
FIG. 1 shows the HPLC chromatogram of eptifibatide provided in example 2.

The present invention discloses a method for preparing eptifibatide, which can be realized by appropriately improving process parameters by those skilled in the art in view of the disclosure. It should be particularly noted that, all similar substitutions and modifications are apparent to those skilled in the art, and all of them are deemed to be encompassed in the present invention. The method and application of the present invention will be described through preferred examples, and those skilled in the art can obviously realize and apply the technology of the present invention by making modifications or appropriate alterations and combinations to the method and application as described herein, without departing from the content, spirit and scope of the present invention.

The invention provides a method for preparing eptifibatide comprising:

step A: obtaining a refined eptifibatide peptide solution;

step B: rotarily evaporating the refined eptifibatide peptide solution, obtaining and freeze-drying a refined eptifibatide peptide concentrate;

wherein the concentration of the refined eptifibatide peptide concentrate is 15-30 mg/mL;

during the rotary evaporation, the temperature of the rotary evaporation is 25° C.-35° C.;

wherein the refined eptifibatide peptide solution is prepared by: obtaining a Cys-resin by coupling Cys to a resin; obtaining a polypeptide having a sequence as represented by SEQ ID NO: 1 by sequentially coupling the Cys-resin with Pro, Trp, Asp, Gly, Har and Mpa; and obtaining the refined eptifibatide peptide solution through oxidation, cleavage, purification and salt conversion.

In order to prevent the further increase of the content of eptifibatide dimer impurities during the concentration, in some examples provided in the present invention, the concentration of the refined eptifibatide peptide concentrate is 15-20 mg/mL.

In order to both guarantee that the organic solvent in the refined eptifibatide peptide concentrate is removed by rotary evaporation in relatively short time, and guarantee that the content of eptifibatide dimer impurities will not further increase, in some examples provided in the present invention, the temperature of rotary evaporation is 30° C.-35° C.

In practical operation, the concentration of the refined eptifibatide peptide concentrate can be controlled by controlling the volume of the organic solvent evaporated during the rotary evaporation. In some examples provided in the present invention, the refined eptifibatide peptide concentrate accounts for 20%-36% by volume of the refined eptifibatide peptide solution.

The present invention provides a method for preparing eptifibatide. The method comprises: obtaining a refined eptifibatide peptide solution; rotarily evaporating the refined eptifibatide peptide solution, obtaining and freeze-drying a refined eptifibatide peptide concentrate; wherein the concentration of the refined eptifibatide peptide concentrate is 15-30 mg/mL; the temperature of the rotary evaporation is 25° C.-35° C.; wherein the refined eptifibatide peptide solution is prepared by obtaining a Cys-resin by coupling Cys to a resin, obtaining a polypeptide having a sequence as represented by SEQ ID NO: 1 by sequentially coupling the Cys-resin with Pro, Trp, Asp, Gly, Har and Mpa, and obtaining the refined eptifibatide peptide solution through oxidation, cleavage, purification and salt conversion. The method of the present invention controls the content of eptifibatide dimer impurities in the refined eptifibatide peptide concentrate to 0.01%-0.09% by controlling the concentration and temperature during the concentration of the eptifibatide solution. The content of the eptifibatide dimer impurities is within the limit for polypeptide impurities as established by FDA and SFDA. Besides, acetonitrile and other organic residues in the refined eptifibatide peptide concentrate meet relevant standards in Chinese Pharmacopoeia. However, in control experiments, when the temperature of rotary evaporation is too low and the concentration of the refined eptifibatide peptide concentrate is relatively low, although the content of the eptifibatide dimer impurities will not increase, the content of acetonitrile in the final product will go beyond the standards remarkably; when the temperature of rotary evaporation is too high and the concentration of the refined eptifibatide peptide concentrate is relatively low or high, the content of eptifibatide dimer impurities in the refined eptifibatide peptide concentrate will go beyond the limit of polypeptide impurities content as established by FDA and SFDA; and when the temperature of rotary evaporation is too low and the concentration of the refined eptifibatide peptide concentrate is relatively low, although the content of eptifibatide dimer impurities will not increase, the content of acetonitrile in the final product will go beyond the standards. It can be seen that the method for preparing eptifibatide of the present invention can significantly reduce the formation of eptifibatide dimer impurities, and besides, allow acetonitrile and other organic residues to meet relevant standards in Chinese Pharmacopoeia.

All the raw materials and reagents used in the method for preparing eptifibatide of the present invention are commercially available.

The invention will be further illustrated below in conjunction with the examples.

Example 1

Preparation of a Refined Eptifibatide Peptide Solution 100.0 g of Sieber resin (having a substitutivity of 0.6 mmol/g) was added to a solid phase reaction column, and the resin was swelled with DMF for 30 min. After complete swelling, Fmoc deprotection was carried out with 20% BDLK (10 min+20 min), and then the column was washed for 6 times with DMF.

49.74 g of Fmoc-Cys(Acm)-OH, 38.52 g of HBTU, 16.2 g of HOBt and 41.8 mL of DIPEA were added to the above solid phase reaction column, and the reaction was carried out for 2 h, and a Fmoc-Cys(Acm)-Sieber resin was obtained.

According to the above method of coupling Fmoc-Cys(Acm)-OH, Fmoc-Pro-OH, Fmoc-Trp-OH, Fmoc-Asp(OtBu)-OH, Fmoc-Gly-OH, Fmoc-Homoarg(pbf)-OH and Acm-Mpa-OH were sequentially coupled onto the Fmoc-Cys(Acm)-Sieber resin. After completion of the coupling, the resin was washed for 3 times with DMF, 3 times with DCM, and shrunk for 3 times with methanol. After drying under vacuum, 172.1 g of an eptifibatide resin with completely protected liner side chains was weighed and obtained.

172.1 g of the eptifibatide resin with completely protected liner side chains was swelled with DMF for 30 min. After complete swelling, 304.8 g of iodine dissolved in an appropriate amount of DMF was added to the reaction column filled with the resin, to perform an oxidization reaction for 2 h. After completion of the reaction, the resin was washed for 10 times with DMF, 3 times with DCM, and shrunk for 3 times with methanol. After drying under vacuum, 164.1 g of an oxidized eptifibatide resin with completely protected side chains was weighed and obtained.

164.1 g of the oxidized eptifibatide resin with completely protected side chains was added to a 3 L round bottom flask, and then 1641 mL of lysate (the ratio of each component in the lysate was: trifluoroacetic acid:water:triisopropylsilane=95:2.5:2.5) was added, for reaction for 2 h. After completion of the lytic reaction, the mixture is filtered, and the filtrate was precipitated with 16.4 L of ice ether, centrifuged, washed, centrifuged again, washed again, centrifuged again, and finally dried under vacuum. 46.9 g of a crude eptifibatide peptide was weighed and obtained.

46.9 g of the crude eptifibatide peptide was purified using a preparative reverse phase HPLC with the following specific procedure.

Purification conditions: chromatographic column: a chromatographic column with octadecylsilane-bonded silica gel as the stationary phase, and the diameter and length of the column was 5 cm×25 cm; In the mobile phase, phase A was 0.1% aqueous solution of trifluoroacetic acid, phase B was acetonitrile; Flow rate: 70-80 mL/min; Detection wavelength: 230 nm; Gradient: B %: 15%-30% (45 min); Injection amount was 1.5-2.0 g.

Purification process: the sample was loaded in a loading amount of 1.5-2.0 g onto the column which had been washed with acetonitrile with a content of above 50% and balanced. It was eluted with a linear gradient for 45 min to collect the peak of interest. The collected solution of the peptide of interest was concentrated to about 10-20 mg/mL by rotary evaporation under reduced pressure at a water temperature of not above 32° C., and was ready for use.

The above purified solution was salinized as follows:

Salinization condition: the chromatographic column was an anion exchange resin (Amberlite IRA-93) with a diameter and length of 5 cm×25 cm; Mobile phase was 0.1-0.3% aqueous solution of acetic acid; Flow rate: 70-80 mL/min; Detection wavelength: 230 nm; Injection amount: 1.5-2.0 g.

Salinization process: the sample was loaded in a loading amount of 100-200 mL sample solution onto the column which had been balanced with deionized water. It was eluted with 0.1-0.3% aqueous solution of acetic acid for 60 min to collect the peak of interest, thus obtaining the refined eptifibatide peptide solution.

The above refined eptifibatide peptide solution was determined for its purity, concentration and volume. The specific process for determining its purity and concentration was as follows:

Preparation of mobile phase A (EP-A mobile phase, 0.085 mol/L potassium dihydrogen phosphate solution:acetonitrile=87:13): 11.6 g of potassium dihydrogen phosphate was weighted out and dissolved homogeneously in 1000 mL of water under stirring. The solution was filtered by suction through a 0.45 μm filter film, and the filtrate was homogeneously mixed with acetonitrile in a ratio of 87:13.

Preparation of mobile phase B (EP-B mobile phase, 0.085 mol/L potassium dihydrogen phosphate solution:acetonitrile=60:40): 11.6 g of potassium dihydrogen phosphate was weighted out and dissolved homogeneously in 1000 mL of water under stirring. The solution was filtered by suction through a 0.45 μm filter film, and the filtrate was homogeneously mixed with acetonitrile in a ratio of 60:40.

Preparation of reference solution R1 (i.e. a solution for determining separation degree): 25 mg of reference eptifibatide was accurately weighed out. Each 2 mg of D-Har-eptifibatide and D-Cys-eptifibatide were weighted out and placed in a 100 mL volumetric flask, which was then added with water to the scale mark to dissolve and dilute the samples, shaken up, thus obtaining a solution containing 0.2 mg/mL of eptifibatideat.

Preparation of reference solution R2 for recovery: 25 mg of reference eptifibatide was accurately weighed out and placed in a 100 mL volumetric flask, which was then added with water to the scale mark to dissolve and dilute the sample, shaken up, thus obtaining a solution containing 0.2 mg/mL of eptifibatide.

Preparation of Sample Solutions for Content Determination:

(1) Preparation of a sample solution before rotary evaporation: 10 mL of sample was accurately weighed out and placed in a 100 mL volumetric flask, which was then added with water for dilution to the scale mark and shaken up; two samples A1, A2 were prepared in duplicate;

(2) Preparation of a sample solution after rotary evaporation: about 2 mL of sample was accurately weighed out and placed in a 100 mL volumetric flask, which was then added with water for dilution to the scale mark and shaken up; two samples A1, A2 were prepared in duplicate.

Preparation of a sample solution for related substances was the same as the preparation of the sample solution for content determination.

Preparation of a reference solution for related substance (1%): 1 mL of sample solution for content determination as described above was accurately weighted out and placed in a 100 mL volumetric flask, which was then added with water for dilution to the scale mark and shaken up.

The purity and concentration of the refined eptifibatide peptide solution were determined by HPLC. Chromatographic conditions: Detection wavelength: λ=220 nm; Flow rate=1.0 mL/min; Injection amount: 20 μL; Chromatographic column with octadecylsilane-bonded silica gel as filler (Intersil ODS-3, 4.6×250 mm, 3 μm); Column temperature: 60° C.; Elution gradient was shown in table 1.

TABLE 1

Table of elution time and elution gradient of HPLC

| | Time (min) | | | | | |
|---|---|---|---|---|---|---|
| | 0 | 30 | 45 | 50 | 50.1 | 55 |
| B (%) | 0 | 0 | 80 | 80 | 0 | 0 |

A system suitability test was firstly performed as follows: 20 μL of reference solution R1 (i.e. the solution for determining separation degree) was injected into the chromatographic instrument, and the chromatogram and main peak area were recorded, with continuous injection for 5 times. The separation degree, average peak area and RSD values were calculated. The standards for the separation degree, average peak area and RSD were that: (1) both the separation degrees between impurity C and eptifibatide and between eptifibatide and impurity D should be more than 2.0 in which impurity C was D-Har-Eptifibatide, impurity D was D-Cys-Eptifibatide; (2) the theoretical plate number calculated according to the main peak of eptifibatide should not be lower than 2000; (3) relative standard deviation (RSD) should be ≤2.0%;

Recovery was determined after the completion of the system suitability test as follows: 20 μL of reference solution R2 for recovery was injected into the chromatographic instrument, and the chromatogram and main peak area were recorded, with continuous injection for 2 times. Recovery was calculated. The standard for recovery was that: recovery should be 98%-102%.

Content determination was performed after the completion of the recovery determination as follows: each 20 μL of sample solutions A1 and A2 were injected into the chromatographic instrument, respectively, with continuous injection for 2 times. The chromatogram and main peak area were recorded, and the content and RSD values were calculated.

The purity and concentration of the refined eptifibatide peptide solution were obtained according to the above method, which were 99.28% (in which the content of dimer impurities was 0.01%) and 6 mg/mL, respectively.

Example 2

Preparation of Eptifibatide

5 L of the refined eptifibatide peptide solution prepared in example 1 was rotarily evaporated at 30° C. During the rotary evaporation, the volume of the rotarily evaporated solution was recorded. The rotary evaporation was stopped when the volume reached up to 3.2 L, which took 1.8 h, thus obtaining a refined eptifibatide peptide concentrate.

The purity, concentration and volume of the above refined eptifibatide peptide concentrate were determined. The purity was 99.28% (in which the content of dimer impurities was 0.01%), the concentration was 15.3 mg/mL, and the total volume was 1.8 L. The HPLC chromatogram was shown in FIG. 1.

The above refined eptifibatide peptide concentrate was still transparent when the rotary evaporation was completed, with no appearance of significant precipitate. The above refined eptifibatide peptide concentrate was freeze-dried to give 29.5 g of eptifibatide. Upon detection, acetonitrile and other organic residues met relevant standards in Chinese Pharmacopoeia. It can be seen that the content of dimer impurities would not further increase under the condition of this concentration and temperature of rotary evaporation. In addition, this temperature of rotary evaporation can make sure that the organic solvent is rotarily evaporated in relatively short time.

Example 3

Preparation of Eptifibatide

5 L of the refined eptifibatide peptide solution prepared in example 1 was rotarily evaporated at 35° C. During the rotary evaporation, the volume of the rotarily evaporated solution was recorded. The rotary evaporation was stopped when the volume reached up to 3.56 L, which took 1.6 h.

Figure 2:
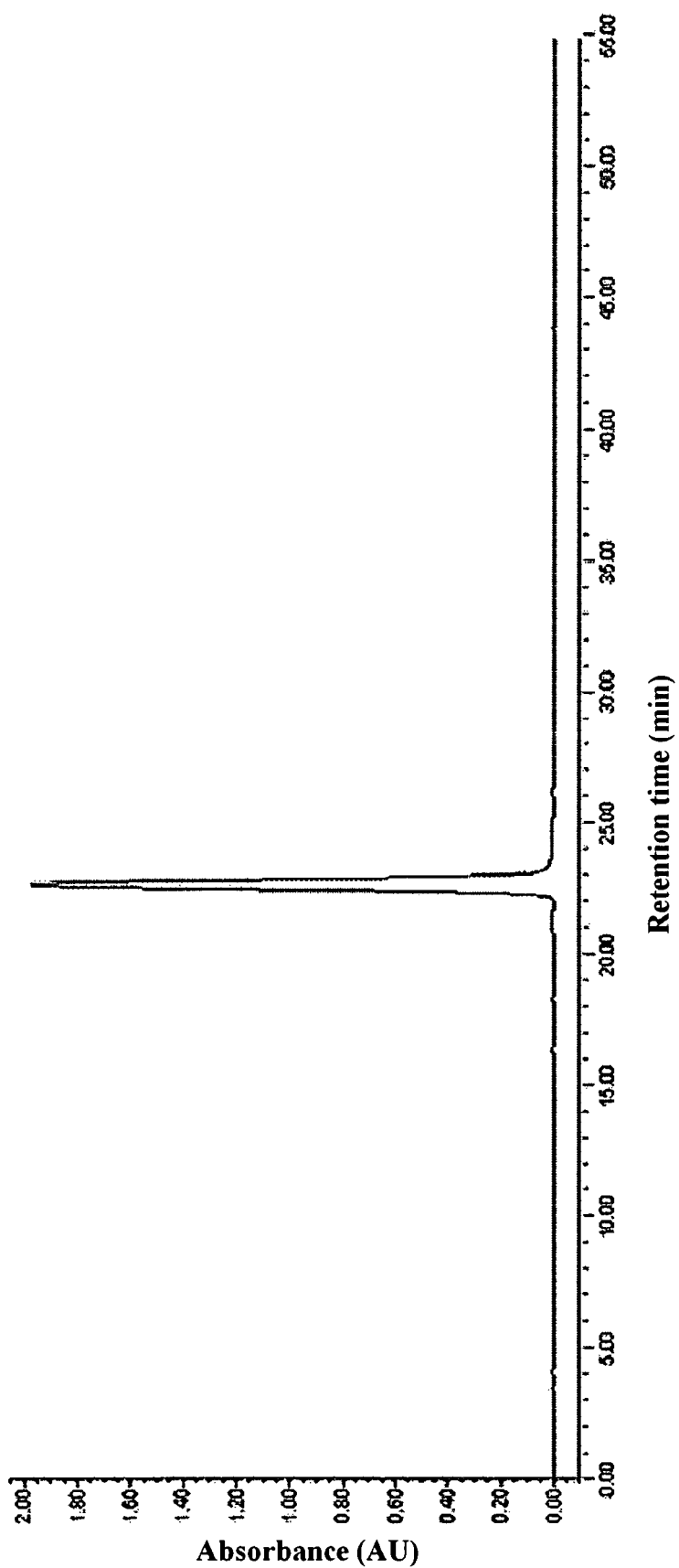
FIG. 2 shows the HPLC chromatogram of eptifibatide provided in example 3.

The purity, concentration and volume of the above refined eptifibatide peptide concentrate were determined. The purity was 99.27% (in which the content of dimer impurities was 0.02%), the concentration was 20.8 mg/mL, and the total volume was 1.44 L. The HPLC chromatogram was shown in FIG. 2.

The above refined eptifibatide peptide concentrate was still transparent when the rotary evaporation was completed, with no appearance of significant precipitate. The above refined eptifibatide peptide concentrate was freeze-dried to give 29.4 g of eptifibatide. Upon detection, acetonitrile and other organic residues met relevant standards in Chinese Pharmacopoeia. It can be seen that the content of dimer impurities would not further increase under the condition of this concentration and temperature of rotary evaporation. In addition, the increased temperature of rotary evaporation accelerated the rate of rotary evaporation.

Example 4

Preparation of Eptifibatide

5 L of the refined eptifibatide peptide solution prepared in example 1 was rotarily evaporated at 30° C. During the rotary evaporation, the volume of the rotarily evaporated solution was recorded. The rotary evaporation was stopped when the volume reached up to 3.79 L, which took 2.2 h.

Figure 3:
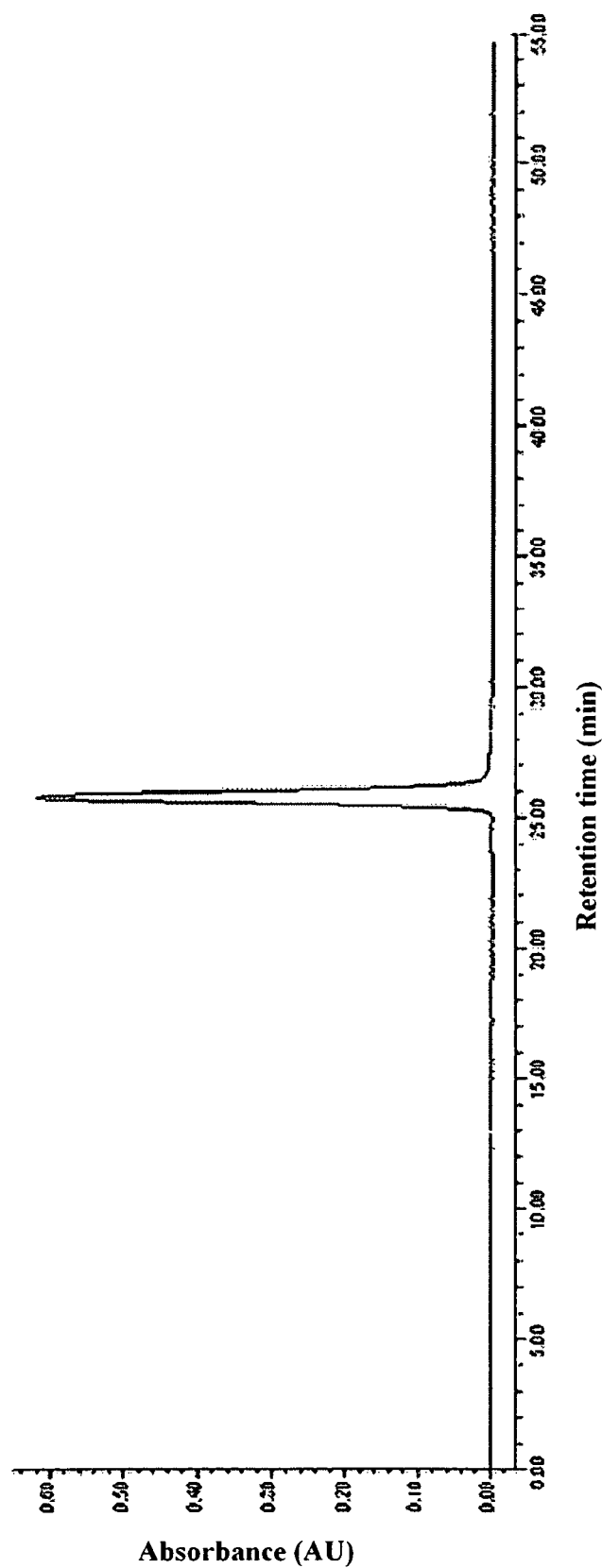
FIG. 3 shows the HPLC chromatogram of eptifibatide provided in example 4.

The purity, concentration and volume of the above refined eptifibatide peptide concentrate were determined. The purity was 99.24% (in which the content of dimer impurities was 0.05%), the concentration was 24.8 mg/mL, and the total volume was 1.21 L. The HPLC chromatogram was shown in FIG. 3.

There was a trace of transparent film-like substance floated on the surface of the above refined eptifibatide peptide concentrate when the rotary evaporation was completed. The above refined eptifibatide peptide concentrate was freeze-dried to give 29.5 g of eptifibatide. Upon detection, acetonitrile and other organic residues met relevant standards in Chinese Pharmacopoeia. The content of dimer impurities was slightly higher than that before rotary evaporation under the condition of this concentration and temperature of rotary evaporation, but was still within the limit of polypeptide impurities as established by FDA and SFDA.

Example 5

Preparation of Eptifibatide

5 L of the refined eptifibatide peptide solution prepared in example 1 was rotarily evaporated at 30° C. During the rotary evaporation, the volume of the rotarily evaporated solution was recorded. The rotary evaporation was stopped when the volume reached up to 3.98 L, which took 2.6 h.

Figure 4:
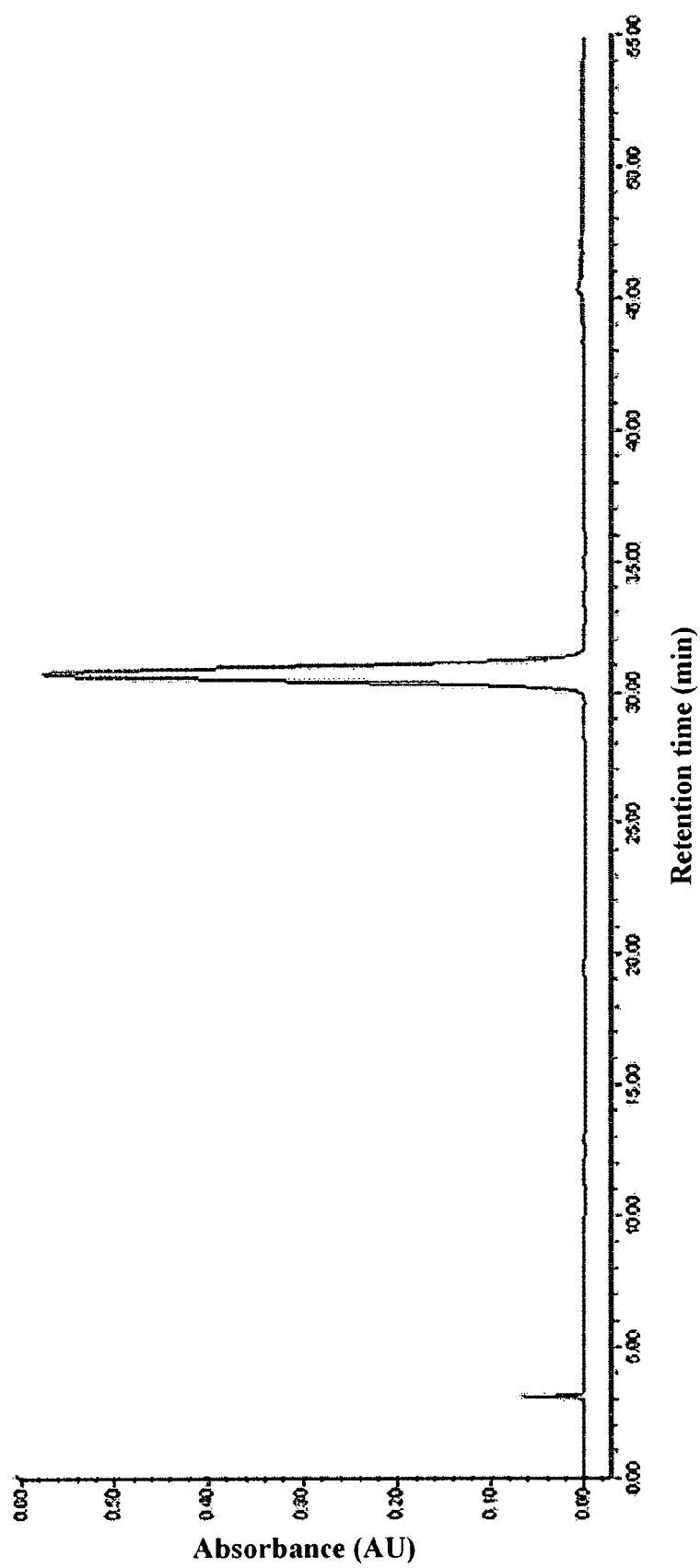
FIG. 4 shows the HPLC chromatogram of eptifibatide provided in example 5.

The purity, concentration and volume of the above refined eptifibatide peptide concentrate were determined. The purity was 99.20% (in which the content of dimer impurities was 0.09%), the concentration was 29.5 mg/mL, and the total volume was 1.02 L. The HPLC chromatogram was shown in FIG. 4.

There was a small amount of transparent film-like substance floated on the surface of the above refined eptifibatide peptide concentrate when the rotary evaporation was completed. The above refined eptifibatide peptide concentrate was freeze-dried to give 29.2 g of eptifibatide. Upon detection, acetonitrile and other organic residues met relevant standards in Chinese Pharmacopoeia. The content of dimer impurities was slightly higher than that before rotary evaporation under the condition of this concentration and temperature of rotary evaporation, but was still within the limit of polypeptide impurities as established by FDA and SFDA.

Example 6

Preparation of Eptifibatide

5 L of the refined eptifibatide peptide solution prepared in example 1 was rotarily evaporated at 33° C. During the rotary evaporation, the volume of the rotarily evaporated solution was recorded. The rotary evaporation was stopped when the volume reached up to 3.44 L, which took 1.8 h.

The purity, concentration and volume of the above refined eptifibatide peptide concentrate were determined. The purity was 99.27% (in which the content of dimer impurities was 0.02%), the concentration was 19.2 mg/mL, and the total volume was 1.56 L.

The above refined eptifibatide peptide concentrate was still transparent when the rotary evaporation was completed, with no appearance of significant precipitate. The above refined eptifibatide peptide concentrate was freeze-dried to give 29.5 g of eptifibatide. Upon detection, acetonitrile and other organic residues met relevant standards in Chinese Pharmacopoeia. It can be seen that the content of dimer impurities would not further increase under the condition of this concentration and temperature of rotary evaporation. In addition, the increased temperature of rotary evaporation accelerated the rate of rotary evaporation.

Example 7

Preparation of Eptifibatide

5 L of the refined eptifibatide peptide solution prepared in example 1 was rotarily evaporated at 25° C. During the rotary evaporation, the volume of the rotarily evaporated solution was recorded. The rotary evaporation was stopped when the volume reached up to 3.60 L, which took 3.7 h.

The purity, concentration and volume of the above refined eptifibatide peptide concentrate were determined. The purity was 99.24% (in which the content of dimer impurities was 0.05%), the concentration was 21.5 mg/mL, and the total volume was 1.40 L.

There was a small amount of transparent film-like substance floated on the surface of the above refined eptifibatide peptide concentrate when the rotary evaporation was completed. The above refined eptifibatide peptide concentrate was freeze-dried to give 29.6 g of eptifibatide. Upon detection, acetonitrile and other organic residues met relevant standards in Chinese Pharmacopoeia. The content of dimer impurities was slightly higher than that before rotary evaporation under the condition of this concentration and tem-

Comparative Example 1

Preparation of Eptifibatide

5 L of the refined eptifibatide peptide solution prepared in example 1 was rotarily evaporated at 20° C. During the rotary evaporation, the volume of the rotarily evaporated solution was recorded. The rotary evaporation was stopped when the volume reached up to 2.06 L, which took 3.2 h.

Figure 5:
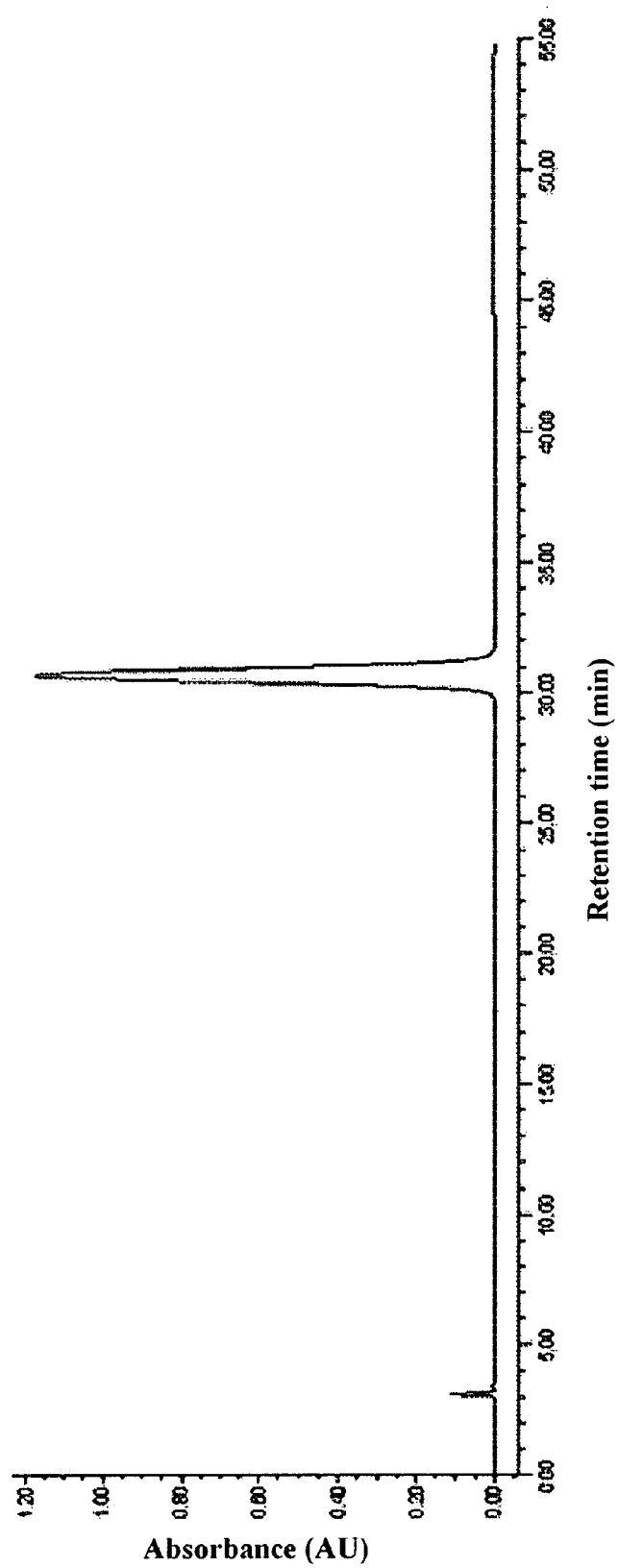
FIG. 5 shows the HPLC chromatogram of eptifibatide provided in comparative example 1.

The purity, concentration and volume of the above refined eptifibatide peptide concentrate were determined. The purity was 99.27% (in which the content of dimer impurities was 0.02%), the concentration was 10.22 mg/mL, and the total volume was 2.94 L. The HPLC chromatogram was shown in FIG. 5.

The above refined eptifibatide peptide concentrate was still transparent when the rotary evaporation was completed, with no appearance of significant precipitate. The above refined eptifibatide peptide concentrate was freeze-dried to give 29.7 g of eptifibatide. Upon detection, the concentration of acetonitrile was 3 times higher than the standard. It can be seen that although the content of dimer impurities was not increased under the condition of this concentration; however, since the temperature of rotary evaporation was too low, the residual organic solvent was excessive, which made acetonitrile in the final product go beyond the standard. In addition, it was very time consuming and not conducive to industrial production.

Comparative Example 2

Preparation of Eptifibatide

5 L of the refined eptifibatide peptide solution prepared in example 1 was rotarily evaporated at 40° C. During the rotary evaporation, the volume of the rotarily evaporated solution was recorded. The rotary evaporation was stopped when the volume reached up to 2.95 L, which took 1.7 h.

The purity, concentration and volume of the above refined eptifibatide peptide concentrate were determined. The purity was 99.14% (in which the content of dimer impurities was 0.15%), the concentration was 14.6 mg/mL, and the total volume was 2.05 L.

There was a large amount of transparent sticky precipitate appearing in the above refined eptifibatide peptide concentrate when the rotary evaporation was completed. The above refined eptifibatide peptide concentrate was freeze-dried to give 29.5 g of eptifibatide. Upon detection, acetonitrile and other organic residues met relevant standards in Chinese Pharmacopoeia. However, the content of dimer impurities was increased to 0.15% from 0.01%. It can be seen that the increased temperature of rotary evaporation accelerated the rate of rotary evaporation, but if the temperature was too high, the content of dimer impurities will be increased as well.

Comparative Example 3

Preparation of Eptifibatide

5 L of the refined eptifibatide peptide solution prepared in example 1 was rotarily evaporated at 40° C. During the rotary evaporation, the volume of the rotarily evaporated solution was recorded. The rotary evaporation was stopped when the volume reached up to 4.04 L, which took 3.1 h.

The purity, concentration and volume of the above refined eptifibatide peptide concentrate were determined. The purity was 99.10% (in which the content of dimer impurities was 0.19%), the concentration was 31.2 mg/mL, and the total volume was 0.96 L.

There was a large amount of transparent sticky precipitate appearing in the above refined eptifibatide peptide concentrate when the rotary evaporation was completed. The above refined eptifibatide peptide concentrate was freeze-dried to give 29.0 g of eptifibatide. Upon detection, acetonitrile and other organic residues met relevant standards in Chinese Pharmacopoeia. However, the content of dimer impurities was increased to 0.19% from 0.01%. It can be seen that the increased temperature of rotary evaporation accelerated the rate of rotary evaporation, but if the temperature was too high, the content of dimer impurities will be increased as well.

The foregoing description is only preferred embodiments of the present invention. It should be noted that various improvements and modifications can be made by those skilled in the art without departing from the principle of the present invention, which should be considered to be within the scope of the present invention.

The invention claimed is:

1. A method for preparing eptifibatide, characterized in comprising:
   (a) obtaining a refined eptifibatide peptide solution;
   (b) rotarily evaporating the refined eptifibatide peptide solution, obtaining and freeze-drying a refined eptifibatide peptide concentrate;
   wherein the concentration of the refined eptifibatide peptide concentrate is 15-20 mg/mL;
   wherein the temperature of the rotary evaporation is 30° C.-35° C.; and
   wherein the refined eptifibatide peptide solution is prepared by obtaining a Cys-resin by coupling Cys to a resin; obtaining a polypeptide having a sequence as represented by SEQ ID NO: 1 by sequentially coupling the Cys-resin with Pro, Trp, Asp, Gly, Har and Mpa; and obtaining the refined eptifibatide peptide solution through oxidation, cleavage, purification and salt conversion.

2. The method according to claim 1, characterized in that the refined eptifibatide peptide concentrate accounts for 20%-36% by volume of the refined eptifibatide peptide solution.

\* \* \* \* \*